United States Patent
Kabanek et al.

Patent Number: 5,152,486
Date of Patent: Oct. 6, 1992

[54] OPERATING ROOM TABLE MATE

[76] Inventors: Joseph R. Kabanek, Rte. 1, Box 1814, Boerne, Tex. 78006-9344; Barbara A. McRee, 14935 Moss Arbor, San Antonio, Tex. 78232

[21] Appl. No.: 685,224

[22] Filed: Apr. 12, 1991

[51] Int. Cl.$^5$ .............................................. F16M 11/00
[52] U.S. Cl. ........................................ 248/201; 108/49
[58] Field of Search ............... 248/201, 447.2; 5/507, 5/508, 82 R, 503, 524; 297/439, 325; 108/49, 32, 1

[56] References Cited

U.S. PATENT DOCUMENTS

| | | | |
|---|---|---|---|
| 623,794 | 4/1899 | Leisenring . | |
| 1,217,676 | 2/1917 | Wilson | 5/507 X |
| 2,569,310 | 9/1951 | Hitt | 108/3 X |
| 2,642,250 | 6/1953 | Kasnowich | 5/507 X |
| 2,703,265 | 3/1955 | Wolfe | 108/49 UX |
| 3,476,256 | 11/1969 | Anderson | 108/49 X |
| 3,545,738 | 12/1970 | Stagg | 269/325 |
| 3,859,993 | 1/1975 | Bitner | 128/847 |
| 4,054,282 | 10/1977 | Hamer | 269/328 |
| 4,113,218 | 9/1978 | Linder | 5/507 X |
| 4,635,914 | 1/1987 | Kabanek | 269/328 |
| 4,747,172 | 5/1988 | Hohol | 248/201 X |

FOREIGN PATENT DOCUMENTS 1404675  10/1968  Fed. Rep. of Germany .......... 5/507

Primary Examiner—J. Franklin Foss
Attorney, Agent, or Firm—Gunn, Lee & Miller

[57] ABSTRACT

A surgical assistance device used by members of the surgical staff as an arm or hand rest, instrument platform or sterile cloth support.

The surgical assistance device is comprised of two rectangular shaped platforms covered by a covering capable of being sterilized. The platforms are attached so that the first platform runs parallel to the patient-supporting surface of the surgical table. The second platform is attached to the first platform and is oriented to the first platform at other than a 180° angle. The bottom surface of the first platform is attached to a mounting means for securing the surgical assistance device to the longitudinal support surface of a surgical table.

16 Claims, 2 Drawing Sheets

OPERATING ROOM TABLE MATE

BACKGROUND OF THE INVENTION

1. Field of the Invention

The invention relates to a surgical assistance device used by a member of a surgical team. The device may be used as an arm support for the surgical assistant, a hand rest for steadying the surgeon's hand, an utility apparatus to hold instruments, or as a drape to hold sterile cloths at elevated heights over the patient.

2. Description of the Prior Art

The prior art consists of surgical attachments used to support an extremity of the patient's body. For instance, apparatuses have been patented that attach to the surgical bed which are used to support a patient's arm or a leg during cleansing and/or the surgical operations, or while taking x-rays of a patient's extremity while the patient is resting on a conventional surgical table.

A distinguishing factor of this invention is that the present invention is not used to support an extremity of the patient's body, rather is used to support the surgeon's or assistant's hands or arms, or used by the surgical staff as a utility apparatus to hold tools or drape sheets over the patient. No invention is known which provides features for use by the surgical staff for support of their extremities.

SUMMARY OF THE INVENTION

The surgical assistance device may be used at the foot, the head, or along the sides of the surgical table. When placed at the head of the surgical table, it is primarily used for surgeries involving the chest, such as open heart surgery, lung surgery, or any other surgeries involving the chest and back.

Because of its unique shape and adjustment capabilities, the surgical assistance device may be used by the surgeon to steady his hand during surgery by providing an arm rest, by a member of the surgical team as an arm support when holding medical instruments which are attached to the patient's body, by the anesthesiologist or anesthetist to elevate drapes above the patient's face to allow vacillation of the face and endotracheal tube to assure proper administration of anesthesia, and as an apparatus to hold instruments while not in use.

It is, therefore, an object of the preset invention to provide a surgical assistance device that can be placed at any position on the surgical table.

It is another object of the present invention to provide a surgical assistance device wherein the angle of support can be adjusted.

It is another object of the present invention to provide a surgical assistance device that can be vertically adjusted.

It is another object of the present invention to provide a surgical assistance device the surgeon can use as an armrest to steady his hand during surgery.

It is another object of the present invention to provide an arm support for a member of the surgical support staff when holding engaged surgical instruments.

It is another object of the present invention to provide the anesthesiologist or the anesthetist a means to elevate drapes above the patient's face for proper vacillation of the face and endotracheal tube to assure proper administration of the anesthesia.

It is another object of the present invention to provide a means wherein instruments may be held while not in use.

It is another object of the invention to provide a support surface that can be sterilized or cleaned easily.

In accordance with the above objectives, applicant's invention is a surgical assistance device that provides a means of support to the surgeon or surgical staff as well as a utility apparatus to hold instruments to or to drape sterile cloths at elevated heights over the patient.

Further advantages of the invention will be readily apparent to those skilled in the art from the following detailed description, taken in conjunction with the annexed sheet of drawings on which is shown a preferred embodiment of the invention.

DESCRIPTION OF THE PREFERRED EMBODIMENT

Figure 1:
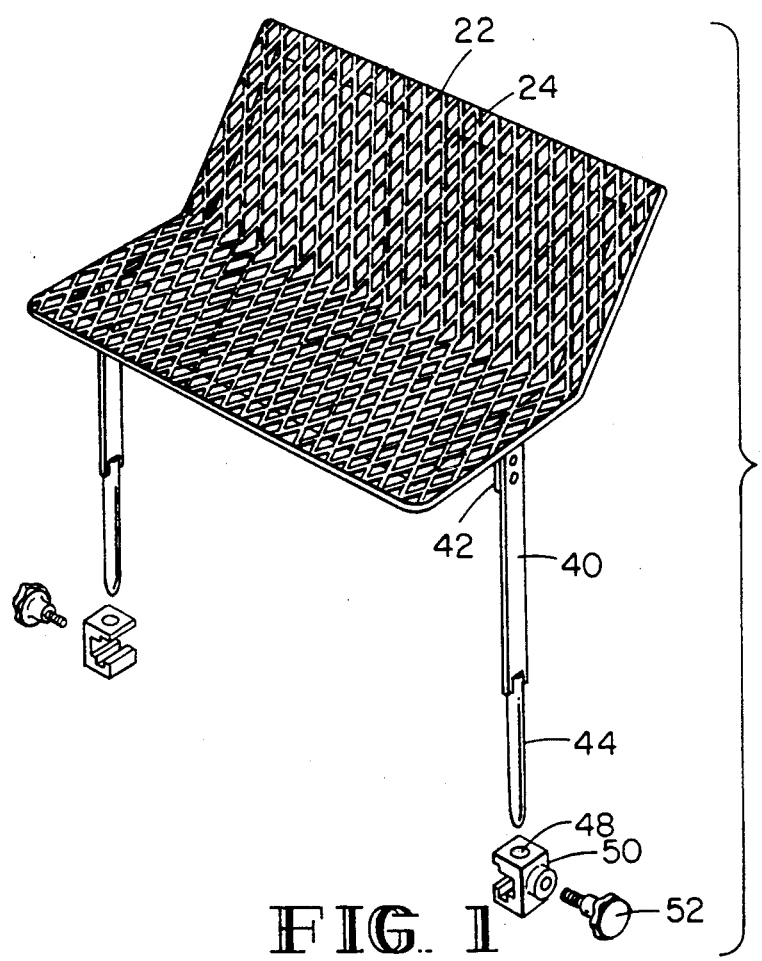
FIG. 1 is a top plan view of the preferred embodiment of the surgical assistance device.
Figure 2:
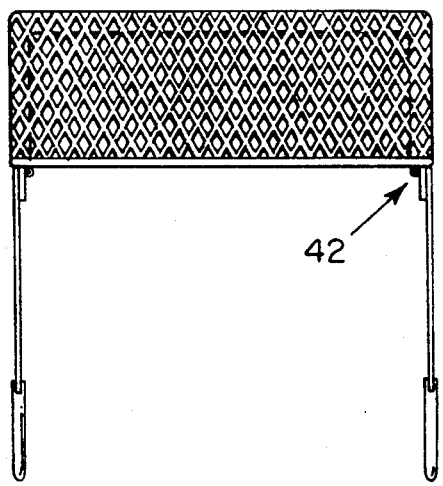
FIG. 2 is a side plan view of the preferred embodiment of the surgical assistance device.
Figure 3:
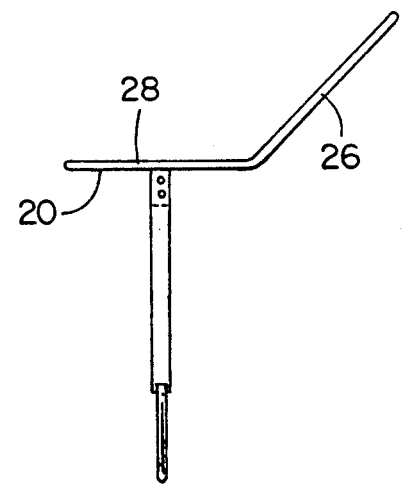
FIG. 3 is a side plan view of the preferred embodiment of the surgical assistance device.

FIG. 1 illustrates the preferred embodiment of the surgical assistance device (10) apart from the surgical table (56) (See FIG. 4) onto which the surgical assistance device (10) is normally mounted. As is customary for surgical tables, they are provided with at least one longitudinal support surface (54) extending the length of one side of the surgical table (56) at a level below, but parallel to the patient support surface (58) of the surgical table (56).

In its preferred embodiment, surgical assistance device (10) is comprised of a pair of mounting shafts (44) and a pair of legs (40) attached to hinges (42). Each hinge (42) is attached to the bottom surface of the frame (20) of the parallel platform (28) of the surgical assistance device (10). A non-sterile covering (22) covers the top surface of both the angled platform (26) and the parallel platform (28). The non-sterile covering (22) is interspersed with passages (24) in a regular pattern.

Figure 4:
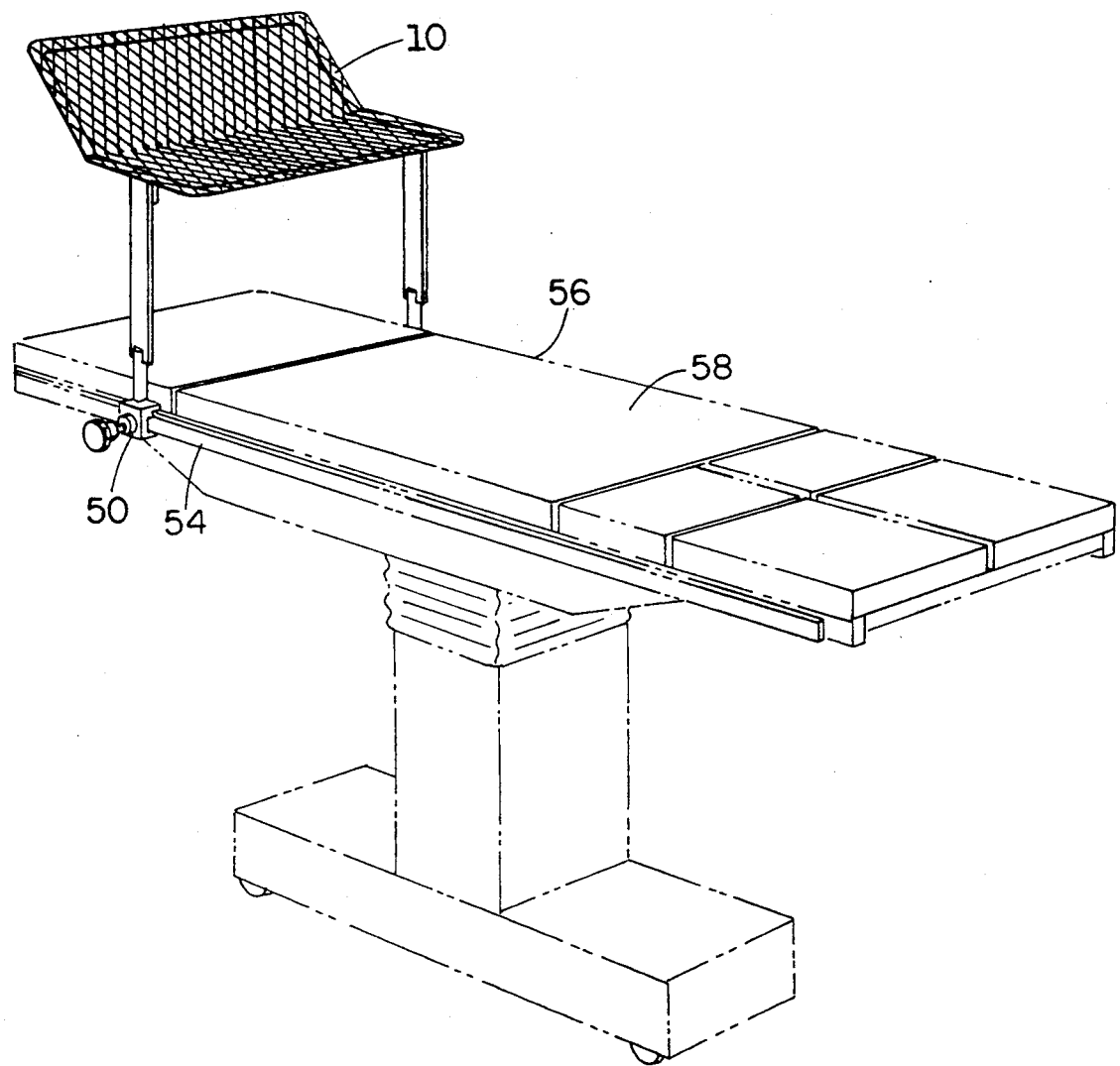
FIG. 4 is a perspective view of the preferred embodiment of the surgical assistance device mounted on top of the surgical table.

FIG. 4 is a perspective view of the preferred embodiment of surgical assistance device (10) firmly mounted on the longitudinally support surface (54) by a pair of C-shaped clamps (50) which encircle the longitudinal support surface (54) and are each provided with a vertically extending slot (48) for receiving therein the mounting shaft (44). A manually operable clamping bolt (52) effects the rigid interengagement of the clamps (50), the longitudinally support surface (54), and the mounting shaft (44).

Although the preferred embodiment of the surgical assistance device (10) as described above, is attached to one end of the surgical table (56), surgical assistance device (10) alternatively may be attached at any position on the longitudinal support surface (54). The vertical position of the surgical assistance device (10) can also be adjusted by the positioning of the mounting shafts (44) in the vertically extending slot (48) of the C-shaped clamps (50).

The surgical assistance device (10) is constructed of a light-weight material that gives both strength and durability. In its preferred embodiment, the surgical assistance device (10) is constructed of honeycomb steel. The non-sterile covering (22) of the surgical assistance device (10) is also constructed of a light-weight yet durable and strong material capable of being cleaned and sterilized such as chrome, silver nitrate or plastics. In its preferred embodiment, the non-sterile covering (22) is made of a plastic coating capable of sterilization.

Although the invention has been described with reference to specific embodiments, this description is not meant to be construed in a limited sense. Various modifications of the disclosed embodiments, as well as alternatives apparent to persons skilled in the art will become apparent upon reference to the description of the invention. It is therefore contemplated that the appended claims will cover such modifications that fall within the scope of the invention.

What is claimed and desired to be secured by Letters Patents is:

1. An arm-supporting apparatus for a member of a surgical team performing an operation on a patient supported on a surgical table having one attachment rail respectively extending along one edge of the surgical table, comprising, in combination:
   an armrest platform having a horizontal planar surface;
   a pair of support bars respectively secured in depending relation to the lateral edges of said armrest platform in substantially vertical alignment with said attachment rail;
   a pair of clamps respectively securable in opposed relation at any selected location along said attachment rail;
   a pair of mounting posts;
   each said mounting post having one end securable in one of said clamps to support the mounting post in generally vertical alignment relative to the attachment rail; and
   means on the top end of each said mounting post for detachable engagement with the bottom end of the respective support bars solely by downward movement of said platform relative to said surgical table, whereby said armrest platform may be removed from the surgical table at any time by upward movement relative to the surgical table.

2. The apparatus of claim 1 wherein said armrest platform further comprises a second planar surface adjacent said first mentioned planar surface and disposed at an upwardly inclined angle relative to said first mentioned planar surface.

3. The invention of claim 12 wherein said armrest platform is covered by a nonsterile covering capable of being cleaned and sterilized.

4. The apparatus of claim 3 wherein said covering is flexible.

5. The apparatus of claim 2 wherein said second planar surface is oriented at a 135° degree angle to said first planar surface.

6. The invention of claim 5 wherein said armrest platform is covered by a nonsterile covering capable of being cleaned and sterilized.

7. The apparatus of claim 6 wherein said covering is flexible.

8. The apparatus of claim 2 wherein said support bars are attached to said lateral edges of said armrest platform by hinges;
   said hinges being attached to the bottom surface of said horizontal planar surface to cause said support bars and said mounting post to fold parallel to said horizontal planar surface when storing said arm-supporting apparatus.

9. An arm-supporting apparatus for a member of a surgical team performing an operation on a patient supported on a surgical table having two attachment rails respectively extending along two opposed edges of the surgical table, comprising, in combination:
   an armrest platform having a horizontal planar surface substantially as wide as the spacing of said two attachment rails;
   a pair of support bars respectively secured in depending relation to the lateral edges of said armrest platform in substantially vertical alignment with said attachment rails;
   a pair of clamps respectively securable in opposed relation at any selected location along said attachment rails;
   a pair of mounting posts;
   each said post having one end securable in one of said clamps to support the mounting post in a generally vertical upstanding position relative to the respective attachment rail; and
   means on the top end of each said mounting post for detachable engagement with the bottom end of the respective support bar solely by downward movement of said platform relative to said surgical table, whereby said armrest platform may be removed from the surgical table at any time by upward movement relative to the surgical table.

10. The apparatus of claim 9 wherein said armrest platform further comprises a second planar surface adjacent said first mentioned planar surface and disposed at an upwardly inclined angle relative to said first mentioned planar surface.

11. The invention of claim 10 wherein said armrest platform is covered by a nonsterile covering capable of being cleaned and sterilized.

12. The apparatus of claim 11 wherein said covering is flexible.

13. The apparatus of claim 10 wherein said second planar surface is oriented at a 135° degree angle to said first planar surface.

14. The invention of claim 13 wherein said armrest platform is covered by a nonsterile covering capable of being cleaned and sterilized.

15. The apparatus of claim 14 wherein said covering is flexible.

16. The apparatus of claim 10 wherein said support bars are attached to said lateral edges of said armrest platform by hinges;
   said hinges being attached to the bottom surface of said horizontal planar surface to cause said support bars and said mounting post to fold parallel to said horizontal planar surface when storing sad arm-supporting apparatus.

* * * * *